United States Patent [19]

Aller

[11] 4,022,890

[45] May 10, 1977

[54] SAFENED PESTICIDAL COMPOSITIONS

[75] Inventor: Harold Ernest Aller, Norristown, Pa.

[73] Assignee: Rohm and Haas Company, Philadelphia, Pa.

[22] Filed: July 7, 1975

[21] Appl. No.: 594,147

[52] U.S. Cl. .............................. 424/225; 424/341; 424/354
[51] Int. Cl.$^2$ ..................... A01N 9/36; A01N 9/02
[58] Field of Search ................. 424/225, 341, 354; 260/964

[56] References Cited

UNITED STATES PATENTS

| | | | |
|---|---|---|---|
| 3,839,511 | 10/1974 | Kishino et al. | 260/964 |
| 3,839,562 | 10/1974 | Chodnekar et al. | 424/224 |
| 3,896,191 | 7/1975 | Drabek | 260/964 |

*Primary Examiner*—V. D. Turner

[57] ABSTRACT

Insecticidal compositions which comprise an O-ethyl S-n-propyl O-halophenyl phosphorothiolate can be safened by adding to the compositions a safening amount of methoxychlor (1,1,1-trichloro-2,2-bis(4-methoxyphenyl)-ethane or 1,1-dichloro-2,2-bis(4-ethylphenyl)ethane. These safened compositions are particularly useful in controlling insects in growing cotton crops.

6 Claims, No Drawings

SAFENED PESTICIDAL COMPOSITIONS

This invention relates to safened insecticidal compositions which comprise an O-ethyl S-n-propyl O-halophenyl phosphorothiolate and which comprise methoxychlor or 1,1-dichloro-2,2-bis(4-ethylphenyl)ethane as a safening agent, and to methods of controlling insects with these compositions.

The use of insecticides in controlling insects in agronomic crops has become a standard worldwide agricultural practice. However, many compounds which have significant insecticidal activity also cause severe injury to many important crops. Consequently, although the compound will successfully control the insects in the crops, the high degree of phytotoxicity caused by the compounds eliminates the possibility of commercial use of the compound on that crop.

It has now been found that insecticidal compositions which comprise an O-ethyl S-n-propyl O-halophenyl phosphorothiolate can be safened so as to limit undesirable phytotoxicity by adding to these compositions a safening amount of methoxychlor (1,1,1-trichloro-2,2-bis(4-methoxyphenyl)ethane or 1,1-dichloro-2,2-bis(4-ethylphenyl)ethane. Generally, in the safened insecticidal compositions of the invention the phosphorothiolate and the methoxychlor or 1,1-dichloro-2,2-bis(4-ethylphenyl)ethane will be combined in a weight ratio (phosphorothiolate : safening agent) of about 2 : 1 to about 1 : 10, and preferably about 1 : 1 to about 1 : 4. Mixtures of methoxychlor or 1,1-dichloro-2,2-bis(4-ethylphenyl)ethane can also be used as the safening agent.

The phosphorothiolates which can be used in the compositions of the invention have the formula

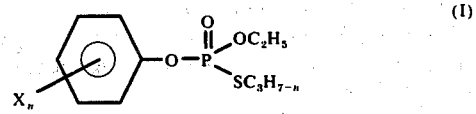

wherein X is a halogen atom preferably bromine or chlorine, and
$n$ is 1, 2 or 3

The preferred phosphorothiolates in the compositions of the invention are O-ethyl S-n-propyl O-2,4,6-trichlorophenyl phosphorothiolate and O-ethyl S-n-propyl O-4-bromo-2-chlorophenyl phosphorothiolate.

The compositions of the invention are useful for controlling insects in a wide variety of crops, including cotton, soybeans, wheat, corn, and the like. However, the compositions are especially useful in cotton. the phosphorothiolate when used alone severly injures the cotton plants. However, when the safening agent is added to the compositions, little or no phytotoxicity is observed. The compositions of the invention are usually applied to the crop at a rate of about 0.5 to about 12 pounds of active ingredient (total phosphorothiolate plus safening agent) per acre, and preferably from about 0.75 to about 5 pounds of active ingredient per acre.

The compositions of the invention are generally applied to the crop to be treated in an agricultural formulation which also comprises an agronomically acceptable carrier. By agronomically acceptable carrier is meant any substance which can be used to dissolve, disperse, or diffuse an active compound in the composition without impairing the effectiveness of the compound and which by itself has no detrimental effect on the soil, equipment, crops, or agronomic environment. The compositions of the invention can be either solid or liquid formulations or solutions. For example, the compounds can be formulated as wettable powders, emulsifiable concentrates, and dusts. In such formulations, the compounds are extended with a liquid or solid carrier and, when desired, suitable surfactants are incorporated.

It is usually desirable to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

For the preparation of emulsifiable concentrates, the active compounds can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent, soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product.

Wettable powders suitable for spraying, can be prepared by admixing the active compounds with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to about 60% by weight. A dispersing agent can constitute about 0.5% to about 3% of the composition, and a wetting agent can constitute from about 0.1% to about 5% of the composition.

Dusts can be prepared by mixing the composition of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to about 60% by weight of the active ingredients are commonly made and are subsequently diluted to about 1% to 10% use concentration.

The compositions of the invention can be applied as sprays by methods commonly employed, such as conventional high-gallonage hydraulic sprays, low gallonage sprays, air-blast spray, aerial sprays and dusts. For low volume applications a solution of the active compounds is usually used. The dilution and rate of application will usually depend upon such factors as the type of equipment employed, the method of application, and the area to be treated.

For some applications, it may be useful to add one or more other insecticides to the compositions of the invention. Examples of other insecticides which can be incorporated to provide additional advantages include parathion, methyl parathion, malathion, carbaryl, methomyl, dicofol, monocrotophos, chlordimeform, and the like. Other pesticides, including fungicides, viricides, and plant bactericides can also be included in the compositions of the invention.

The following examples will further illustrate this invention but will not intend to limit it in any way. All parts and percentages are by weight unless otherwise indicated.

EXAMPLE 1

This example demonstrates the safening effect of combining methoxychlor with O-ethyl S-n-propyl O-2,4,6-trichlorophenyl phosphorothiolate (Compound A) in insecticidal compositions.

Three weeks after planting, cotton plants are sprayed to runoff with a manually held atomizer with formulated insecticidal compositions (prepared from emulsifiable concentrates and/or wettable powders) containing various rates (lb/100 gal. approximately equal to lb/acre in field applications) of the phosphorothiolate (one part) and methoxychlor (four parts). Three days after treatment, the phytotoxicity of the compositions is rated on a scale of 0 (no injury) to 5 (dead plant). The following Table I summarizes the results of these tests.

TABLE I

| Compound A (lb/100 gal) | Cotton Phytotoxicity Methoxychlor (lb/100 gal) | Phytotoxicity |
|---|---|---|
| 2 | — | 4.3 |
| — | 8 | 0 |
| 2 | 8 | 1.7 |
| 1 | — | 3.2 |
| — | 4 | 0 |
| 1 | 4 | 0.5 |
| 0.5 | — | 1.3 |
| — | 2 | 0 |
| 0.5 | 2 | 0.2 |
| 0.25 | — | 1.2 |
| — | 1 | 0 |
| 0.25 | 1 | 0 |

Other ratios of Compound A to methoxychlor (including 1 : 2 and the like) can also be used to obtain a desirable safening effect.

EXAMPLE 2

This example shows the effectiveness of 1,1-dichloro-2,2-bis(4-ethylphenyl)ethane (Compound B) for safening insecticidal compositions which comprise O-ethyl S-n-propyl O-2,4,6-trichlorophenyl phosphorothiolate.

Following the procedure of Example 1, three-week old cotton plants are treated with various insecticidal compositions containing O-ethyl S-n-propyl O-2,4,6-trichlorophenyl phosphorothiolate (Compound A) and 1,1-dichloro-2,2-bis(4-ethylphenyl)ethane as an emulsifiable concentrate in 1 : 4 and 1 : 2 weight ratios. Table II summarizes the results of these tests.

TABLE II

| Compound A (lb/100 gal) | Cotton Phytotoxicity CompoundB (lb/100 gal) | Phytotoxicity |
|---|---|---|
| 2 | — | 2.8 |
| 1 | — | 1.8 |
| 0.5 | — | 1.0 |
| 0.25 | — | 0.5 |
| — | 8 | 0 |
| — | 4 | 0 |
| — | 2 | 0 |
| — | 1 | 0 |
| — | 0.5 | 0 |
| 2 | 8 | 0.7 |
| 2 | 4 | 0.8 |
| 1 | 4 | 0.2 |
| 1 | 2 | 0.2 |
| 0.5 | 2 | 0 |
| 0.5 | 1 | 0 |
| 0.25 | 1 | 0 |
| 0.25 | 0.5 | 0 |

Other ratios of Compound A to 1,1-dichloro-2,2-bis(4-ethylphenyl)ethane (including 1 : 1 and the like) can also be used to obtain a desirable safening effect.

The compositions of the invention also retain the high degree of insecticidal activity possessed by the individual components of the compositions.

It is to be understood that changes and variations may be made without departing from the spirit and scope of the invention as defined by the appended claims.

I claim:

1. A safened insecticidal composition which comprises an insecticidally-effective amount of O-ethyl S-n-propyl O-2,4,6-trichlorophenyl phosphorothiolate and, as a safening agent, an amount effective to limit phytotoxicity of methoxychlor or 1,1-dichloro-2,2-bis(4-ethylphenyl)ethane, wherein the weight ratio of the phosphorothiolate to the safening agent is about 1:2 to about 1:4.

2. The composition of claim 1 wherein the safening agent is methoxychlor.

3. The composition of claim 1 wherein the safening agent is 1,1-dichloro-2,2-bis(4-ethylphenyl)ethane.

4. The composition of claim 1 which additionally comprises an agronomically-acceptable carrier and a surfactant.

5. A method of controlling insects in cotton which comprises applying to the cotton a composition according to claim 1 in an insecticidally effective amount.

6. The method of claim 5 wherein the composition is applied at a rate of about 0.5 to about 12 pounds of total phosphorothiolate plus safening agent per acre.

* * * * *